United States Patent
Choi et al.

(10) Patent No.: US 10,801,779 B2
(45) Date of Patent: Oct. 13, 2020

(54) METHOD FOR FORMING NANOPORES

(71) Applicant: KOREA UNIVERSITY RESEARCH AND BUSINESS FOUNDATION, Seoul (KR)

(72) Inventors: Wonjoon Choi, Seoul (KR); Tae Young Park, Busan (KR)

(73) Assignee: Korea University Research and Business Foundation, Seoul (KR)

( * ) Notice: Subject to any disclaimer, the term of this patent is extended or adjusted under 35 U.S.C. 154(b) by 260 days.

(21) Appl. No.: 15/958,328

(22) Filed: Apr. 20, 2018

(65) Prior Publication Data

US 2018/0274861 A1 Sep. 27, 2018

(30) Foreign Application Priority Data

Feb. 28, 2017 (KR) .................. 10-2017-0026404

(51) Int. Cl.
  *G01N 33/487* (2006.01)
  *F27D 5/00* (2006.01)

(52) U.S. Cl.
  CPC ..... *F27D 5/0006* (2013.01); *G01N 33/48721* (2013.01); *F27M 2003/15* (2013.01)

(58) Field of Classification Search
  CPC .............................................. G01N 33/48721
  USPC ....................................................... 438/610
  See application file for complete search history.

(56) References Cited

U.S. PATENT DOCUMENTS

| 8,921,473 | B1 * | 12/2014 | Hyman ............... | C08K 3/04 423/445 R |
| 2008/0176074 | A1 * | 7/2008 | Lee .................. | B29C 67/08 428/402 |
| 2014/0064324 | A1 * | 3/2014 | Kasianowicz ........ | G01K 7/16 374/45 |
| 2015/0241418 | A1 * | 8/2015 | Wolfrum ............. | B82Y 40/00 428/315.5 |

FOREIGN PATENT DOCUMENTS

| JP | 2005-233637 A | 9/2005 |
| KR | 10-2009-0121544 A | 11/2009 |

OTHER PUBLICATIONS

Vreede, Lennart J. de, et al., "Nanopore Fabrication by Heating Au Particles on Ceramic Substrates", *Nano Letters*, Dec. 30, 2014, pp. 1-8, vol. 15.1.

* cited by examiner

*Primary Examiner* — Jami Valentine Miller
(74) *Attorney, Agent, or Firm* — NSIP Law

(57) ABSTRACT

Disclosed is a method for forming nanopores. The method includes (A) preparing a dispersion of gold nanoparticles (S100), (B) dipping a membrane in the dispersion to attach the gold nanoparticles to the surface of the membrane (S200), and (C) heating the membrane attached with the gold nanoparticles to a predetermined processing temperature such that the surface layers of the gold nanoparticles are liquefied and evaporated, to form nanopores with predetermined shapes on the membrane (S300).

11 Claims, 4 Drawing Sheets

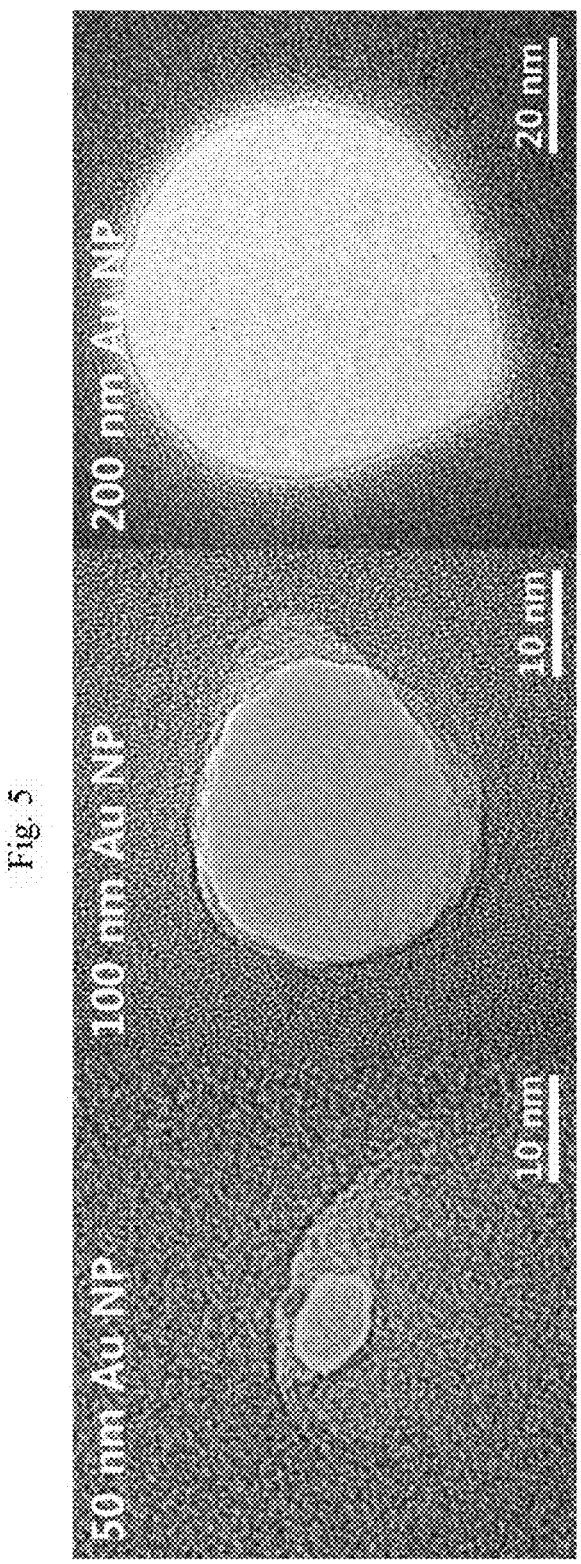

METHOD FOR FORMING NANOPORES

CROSS-REFERENCE TO RELATED APPLICATIONS

This application claims the benefit under 35 USC 119(a) of Korean Patent Application No. 10-2017-0026404 filed on Feb. 28, 2017 in the Korean Intellectual Property Office, the entire disclosure of which is incorporated herein by reference for all purposes.

BACKGROUND OF THE INVENTION

1. Field of the Invention

The present invention relates to a method for forming nanopores, and more specifically to a method for forming nano-sized pores with different shapes based on specific behaviors of gold nanoparticles on a membrane.

2. Description of the Related Art

In recent years, nanopores have been utilized as tools to detect target biomolecules such as DNA and protein molecules in samples. According to a method for DNA detection using nanopores, a voltage is applied to a membrane through which nanopores penetrate, DNA is allowed to pass through the membrane, and changes in current pulse or blockage current are measured to analyze the characteristics (e.g., length and structure) of the DNA.

Nanopores can be broadly classified into biological nanopores and solid-state nanopores. Various biological nanopores composed of proteins, typified by α-hemolysin, are used for research applications. Such biological nanopores have the advantage of very small and uniform pore size but are disadvantageous in that their constituent proteins tend to be denatured by such factors as temperature and pH. In view of this disadvantage, highly stable solid-state nanopores were fabricated.

Many methods for fabricating solid-state nanopores have been developed. For example, Korean Patent Publication No. 10-2009-0121544 A discloses a method for forming solid-state nanopores, including irradiating a first electron beam onto a membrane to form holes in the membrane and irradiating a second electron beam onto the holes to reduce the size of the holes wherein the second electron beam has a lower energy than the first electron beam. This method can be precisely controlled but has the problems of slow processing speed, high cost, and difficult control over the shape of nanopores.

Other methods for forming nanopores based on track etching and dielectric breakdown are also known. Track etching is a process in which a beam is used to damage a membrane and etching is subsequently performed to form pores with a uniform size. However, track etching has the disadvantages that some components of the membrane are replaced by chemical reactions and unintended locations are etched, resulting in low quality. Dielectric breakdown is a process in which a voltage is applied in a solution containing ions to induce dielectric breakdown. Dielectric breakdown is advantageous in that nanopores can be formed at low cost but has the problems that the diameters of formed nanopores cannot be made larger than 25 nm.

Thus, there is an urgent need to find a solution to the problems encountered in conventional methods for forming nanopores.

SUMMARY OF THE INVENTION

The present invention has been made in an effort to solve the problems of the prior art, and it is one aspect of the present invention to provide a method for forming nanopores with different shapes in a desired distribution on a membrane by controlling the size and density of gold nanoparticles arranged on the membrane, controlling the contact time of the gold nanoparticles with the membrane, and inducing specific behaviors of the gold nanoparticles.

A method for forming nanopores according to the present invention includes (A) preparing a dispersion of gold nanoparticles, (B) dipping a membrane in the dispersion to attach the gold nanoparticles to the surface of the membrane, and (C) heating the membrane attached with the gold nanoparticles to a predetermined processing temperature such that the surface layers of the gold nanoparticles are liquefied and evaporated, to form nanopores with predetermined shapes on the membrane.

In the method of the present invention, step (A) includes preparing a dispersion of gold nanoparticles in an aqueous sodium citrate solution and adding dilute hydrochloric acid to the dispersion to prepare a solution of the nanoparticles at a pH of 3.0 or less.

In the method of the present invention, the membrane is a silicon nitride (SiN) or silicon oxide ($SiO_2$) membrane.

The method of the present invention further includes treating the membrane with an oxygen plasma to clean the membrane before step (B).

The method of the present invention further includes washing the membrane attached with the gold nanoparticles with distilled water after step (B) and prior to step (C).

In the method of the present invention, the processing temperature is from 950 to 1060° C.

In the method of the present invention, the nanopores have conical shapes whose cross-section decreases gradually from one surface of the membrane attached with the gold nanoparticles to the other surface thereof and penetrate the membrane to form open shapes or are recessed from the membrane to form closed shapes; and the gold nanoparticles remain attached to the inner surfaces of the nanopores or portions of the one surface of the membrane or are completely removed.

In the method of the present invention, the nanopores are formed in different shapes by at least one factor selected from the diameter of the gold nanoparticles, the thickness of the membrane, and the processing temperature.

In the method of the present invention, when the diameter of the gold nanoparticles is at least 1.5 times larger than the thickness of the membrane, the gold nanoparticles remain attached to portions of the one surface of the membrane.

The features and advantages of the present invention will become apparent from the following description with reference to the accompanying drawings.

Prior to the detailed description of the invention, it should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method.

According to the method of the present invention, the distribution of the gold nanoparticles arranged on the membrane can be controlled in a simple manner by varying the size and density of the gold nanoparticles dispersed in the sodium citrate solution, the pH of the solution, and the contact time of the gold nanoparticles with the membrane.

In addition, the method of the present invention enables the fabrication of conical nanopores, which could not be achieved by conventional methods. Furthermore, the method of the present invention enables the formation of nanopores with different shapes by varying the sizes of the membrane and the gold nanoparticles, the heating temperature, and the processing time according to intended applications.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 4 and 5 are images showing nanopores formed by a method of the present invention.

DETAILED DESCRIPTION OF THE INVENTION

Figure 1:
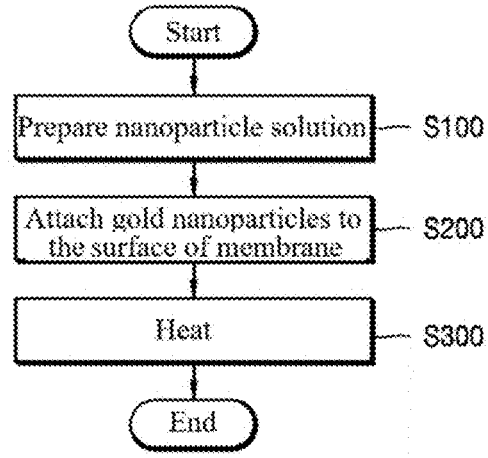
FIG. 1 is a flow chart illustrating a method for forming nanopores according to one embodiment of the present invention.

Other objects, advantages, and novel features of the invention will become more apparent from the following detailed description and preferred embodiments with reference to the appended drawings. In the drawings, the same elements are denoted by the same reference numerals even though they are depicted in different drawings. Although such terms as "first" and "second," etc. may be used to describe various elements, these elements should not be limited by above terms. These terms are used only to distinguish one element from another. In the description of the present invention, detailed explanations of related art are omitted when it is deemed that they may unnecessarily obscure the essence of the present invention.

Preferred embodiments of the present invention will now be described in detail with reference to the accompanying drawings.

Figure 2:
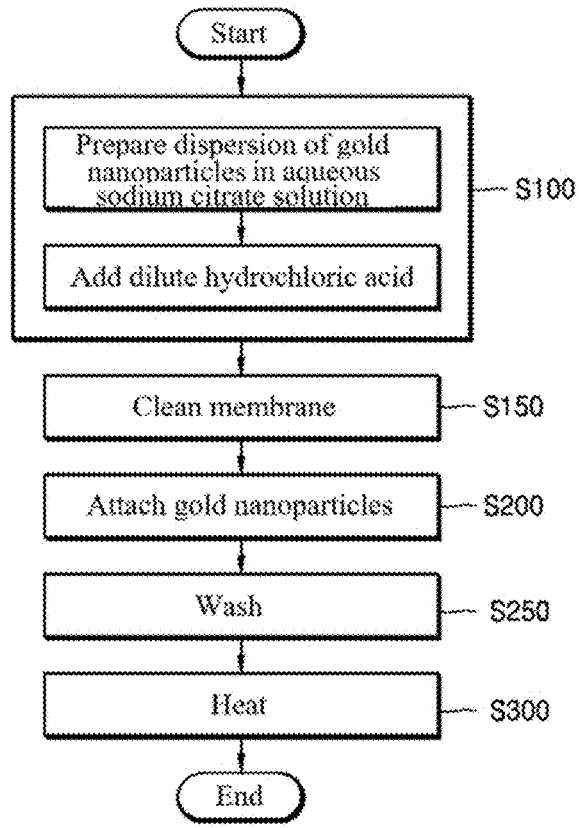
FIG. 2 is a flow chart illustrating a method for forming nanopores according to a further embodiment of the present invention.
Figure 3A:
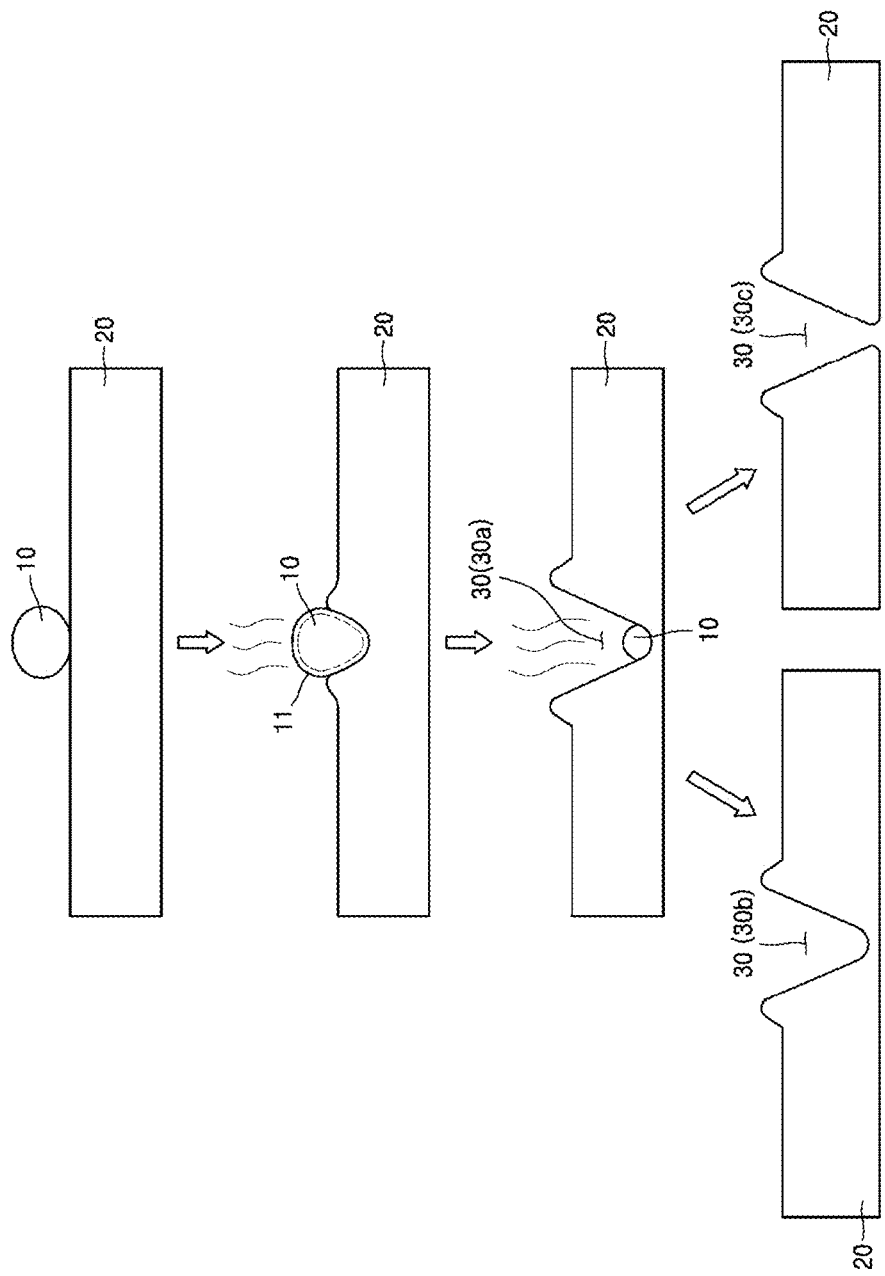
FIGS. 3a and 3b are cross-sectional views illustrating the formation of nanopores by a method of the present invention.
Figure 3B:
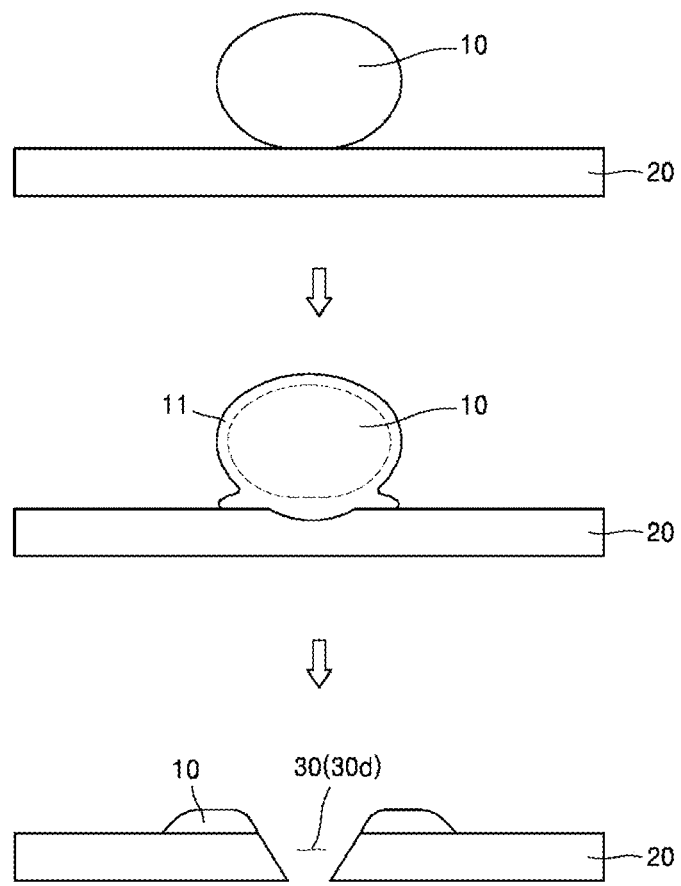

FIG. 1 is a flow chart illustrating a method for forming nanopores according to one embodiment of the present invention, FIG. 2 is a flow chart illustrating a method for forming nanopores according to a further embodiment of the present invention, and FIGS. 3a and 3b are cross-sectional views illustrating process flow diagrams of methods for forming nanopores according to exemplary embodiments of the present invention.

As illustrated in FIGS. 1 and 2, a method for forming nanopores according to the present invention includes (A) preparing a dispersion of gold nanoparticles (S100), (B) dipping a membrane in the dispersion to attach the gold nanoparticles to the surface of the membrane (S200), and (C) heating the membrane attached with the gold nanoparticles to a predetermined processing temperature such that the surface layers of the gold nanoparticles are liquefied and evaporated, to form nanopores with predetermined shapes on the membrane (S300).

The method of the present invention is related to the formation of fine nanopores on a membrane based on gold nanoparticles. Nanoporous membranes can be used in various applications, including DNA sequencing, molecular detection, molecular separation, AFM tip fabrication, and desalination. Conventional methods for forming nanopores are based on etching or dissolution of membranes using particles or high-energy ion beams, track etching wherein beams are used to damage membranes and etching is subsequently performed, and dielectric breakdown wherein a voltage is applied in a solution containing ions to induce dielectric breakdown. However, the irradiation of high-energy beams needs much processing time and incurs a considerable processing cost. Track etching has the disadvantages that the components of membranes are replaced by chemical reactions and nanopores cannot be formed at unintended locations. Dielectric breakdown has the problems that the diameters of formed nanopores cannot be made larger than 25 nm. The method of the present invention can provide solutions to the problems of the prior art.

Nanopores formed by the method of the present invention are broadly divided into four nanopores according to their shapes: nanopores having inner surfaces to which gold remains attached, nanopores in which gold remains attached to portions of one surface of the membrane, open nanopores without gold, and closed nanopores without gold.

The individual steps of the method according to the present invention will be described in detail below.

In step S100, first, gold nanoparticles are dispersed in an aqueous solution containing a surfactant. The surfactant surrounds the gold nanoparticles having a diameter of tens to hundreds of nanometers. Thus, the gold nanoparticles are dispersed without aggregation in the aqueous solution.

Specifically, the surfactant may be sodium citrate. The surfactant prevents the gold nanoparticles from aggregating.

The pH of the aqueous solution is required to have a predetermined pH at which the zeta potential of a membrane is changed, which will be described below. The pH may be, for example, 3.0 or less. The pH is determined from a relationship with the membrane and may vary depending on the material for the membrane. Dilute hydrochloric acid (HCl) may be added to lower the pH of the aqueous solution. The addition of dilute hydrochloric acid allows a portion of the surfactant (e.g., sodium citrate) to be separated from the gold nanoparticles in the aqueous solution, leading to a change in zeta potential. The resulting solution is referred to as a "nanoparticle solution". The zeta potential is still negative. The surfactant remains bound to the gold nanoparticles and is removed in the subsequent heating step.

Next, a membrane is dipped in the nanoparticle solution to attach the gold nanoparticles to the surface of the membrane (S200). The membrane may be a silicon nitride (SiN) or silicon oxide ($SiO_2$) membrane. When the membrane is brought into contact with the nanoparticle solution at a pH of 3.0 or less, for example, about 1 to about 2, the zeta potential of the membrane is changed from negative to positive. Since the zeta potential of the gold nanoparticles is still negative, the silicon nitride or silicon oxide membrane attracts the gold nanoparticles, and as a result, the gold nanoparticles are attached to the surface of the membrane. Based on this principle, the distribution of the gold nanoparticles on the membrane can be controlled by varying the density of the gold nanoparticles in the nanoparticle solution and the contact time between the membrane and the nanoparticle solution. Further, the distribution of the gold nanoparticles may vary depending on the size of the gold nanoparticles.

Lithography has been used to locate gold nanoparticles on membranes. However, lithography involves complex processing steps, including coating of a photoresist on a membrane, arrangement of a mask thereon, irradiation of a laser to cure or remove the photoresist, removal of the mask, sputtering of gold (Au), and etching of remaining photoresist. In contrast, the method of the present invention is based on the attachment of gold nanoparticles, which is relatively simple to perform and has an advantage in that the distribution of the gold nanoparticles can be controlled.

Finally, the gold nanoparticles arranged in a desired distribution on the membrane are heated to a predetermined processing temperature using a heater or CVD apparatus (S300). Gold nanoparticles having a size of about 10 nm or less begin to melt at a lower temperature than their melting point (1063° C.). Particularly, since the gold nanoparticles attached to the silicon nitride or silicon oxide membrane are melted at a lower temperature, the processing temperature is typically set to 950 to 1060° C., which is a temperature around the melting point of gold nanoparticles. However, the processing temperature is not limited and may be determined considering various factors, such as the size of the gold nanoparticles and the material for the membrane.

The gold nanoparticles begin to melt at the processing temperature where the surface atomic layers of the gold nanoparticles are changed to liquid layers. While the processing temperature is maintained, the cores of the gold nanoparticles are in a solid state but the thin surface atomic layers are liquefied and evaporated gradually at the initial stage of heating, and finally the gold nanoparticles are completely evaporated and disappear. In the course of heating, nanopores are formed in the membrane, which will be described below.

According to the method of the present invention, the membrane may be cleaned (S150) before dipping of the membrane in the nanoparticle solution (S200). The membrane may be cleaned by treatment with an oxygen plasma to remove organic matter attached to the surface of the silicon nitride or silicon oxide membrane. That is, this cleaning is effective in attaching the gold nanoparticles.

The method of the present invention may further include washing the membrane (S250). The washing step is carried out after the attachment of the gold nanoparticles (S200) to the membrane and before the formation of nanopores (S300). Specifically, the membrane attached with the gold nanoparticles is washed by rinsing with distilled water. The gold nanoparticles are attached randomly in a predetermined distribution to the membrane by electrical attraction. The membrane is rinsed with distilled water about 10 seconds after attachment of the gold nanoparticles. The distilled water dissolves impurities (including the surfactant in the aqueous solution) other than the gold nanoparticles. Then, the dissolved impurities are removed together with the distilled water.

The surfactant is not necessarily limited to sodium citrate and the aqueous solution may include any aqueous solution known in the art that is capable of dispersing gold nanoparticles and has a negative zeta potential at a pH of 3 or less and from which a surfactant can be removed by distilled water.

Hereinafter, an explanation will be given regarding three shapes of nanopores and conditions for creating the shapes.

Figure 4:
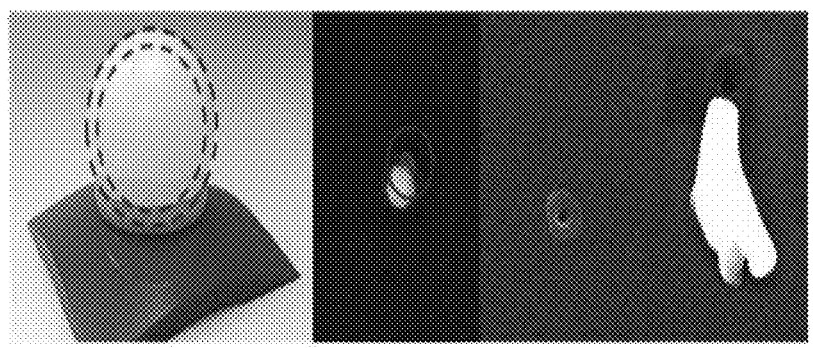

FIGS. 3a and 3b are cross-sectional views illustrating the formation of nanopores by the method of the present invention. FIGS. 4 and 5 are images showing nanopores formed by the method of the present invention.

Nanopores formed by the method of the present invention are broadly divided into four nanopores according to their shapes: open nanopores without gold, closed nanopores without gold, nanopores having inner surfaces to which gold remains attached, and nanopores in which gold remains attached to portions of one surface of the membrane. Each of the nanopores has a conical shape whose cross-section decreases gradually from one surface of the membrane attached with the gold nanoparticles to the other surface thereof.

As illustrated in FIG. 3a, the core of a gold nanoparticle 10 is not completely liquefied at a processing temperature and a liquid layer 11 is formed only in the surface portion of the gold nanoparticle. While the processing temperature is maintained, the liquid layer 11 ascends along the surface of the gold nanoparticle 10. At this time, the surface atoms of a membrane 20 in contact with the gold nanoparticle 10 move along the particle layer of the gold nanoparticle 10. As a result, the peripheral portion of the location of the membrane 20 where the gold nanoparticle 10 is arranged protrudes convexly outward and the central portion thereof forms a concavely recessed conical nanopore 30. The size of the gold nanoparticle 10 decreases and the depth of the nanopore 30 increases with the passage of time. When the gold nanoparticle 10 is completely evaporated, the formation of the nanopore 30 is completed.

In the case where heating is stopped before complete evaporation of the gold nanoparticle 10, a nanopore 30a to which gold, i.e. the gold nanoparticle 10, remain attached is formed. The nanopore 30a does not penetrate the membrane 20 and is concavely recessed to form a closed shape.

When the gold nanoparticle 10 is completely evaporated, the process is completed. In this case, the nanopore 30a may have a closed shape 30b or an open shape 30c penetrating the membrane 20. In either case, the gold disappears completely from the nanopore 3 without being attached to the inner surface of the nanopore 30.

Based on this principle, the nanopore 30a in which gold is present, the closed nanopore 30b or the open nanopore 30c can be selectively formed depending on the diameter (size) of the gold nanoparticle 10, the thickness of the membrane 20, the processing temperature, and the processing time. That is, since the formation of the nanopore 30 is completed when the gold nanoparticle 10 is completely evaporated, the nanopore 30a in which gold is present is changed to the open nanopore 30c as the size of the nanoparticle, the thickness of the membrane 20, the processing temperature, and the processing time increase. The diameter of the gold nanoparticle 10, the thickness of the membrane 20, the processing temperature, and the processing time are factors complementary to each other. Thus, by controlling one or more of these factors, the shape of the nanopore 30 may be determined.

The nanopore 30 in which gold is attached to one surface of the membrane will be explained with reference to FIG. 3b.

For the formation of the nanopore 30 in which gold is attached to one surface of the membrane, the diameter of the gold nanoparticle 10 is required to be at least 1.5 times larger than the thickness of the membrane 20. In this case, the gold nanoparticle 10 is liquefied and evaporated and becomes smaller gradually by continuous heating at the processing temperature, with the result that the melting point of the gold nanoparticle 10 is lowered. Due to the lowered melting point, the core of the gold nanoparticle 10 is also liquefied, and as a result, the gold nanoparticle 10 fails to maintain its original round shape and collapses laterally. That is, droplets are formed in portions of the surface liquid layer 11 of the gold nanoparticle 10 and flow laterally. Even when liquefied, some of the gold atoms are blocked by the lateral side of the nanopore 30 and do not flow laterally any more. The gold atoms are continuously evaporated and the nanopore 30 is formed deeper. The gold nanoparticle 10 is evaporated, finally leaving the gold atoms in portions of one surface of the membrane 20, unlike in the embodiment illustrated in FIG. 3a. That is, some of the gold atoms remain attached to one surface of the membrane 20 even after completion of the process because the mount of the gold atoms flowing laterally is larger than the amount of the gold atoms that depress the membrane 20 to form the nanopore 30.

Also in this embodiment, the shape of the gold-attached nanopore 30 is affected by the diameter of the gold nanoparticle 10, the thickness of the membrane 20, the processing temperature, and the processing time. Accordingly, even when the diameter of the gold nanoparticle 10 is 1.5 times or more larger than the thickness of the membrane 20, an open nanopore 30d without gold or a closed nanopore without gold (not illustrated) may also be formed by controlling the processing temperature and time. However, when it is desired to form the gold-attached nanopore 30, the nanoparticle is required to have an at least 1.5 times larger diameter than the thickness of the membrane 20 despite other conditions.

The gold-attached nanopore 30 may be formed in a closed shape (not illustrated) but is formed in an open shape 30d penetrating the membrane 20 because the thickness of the membrane 20 is much smaller than the size of the gold nanoparticle 10.

Overall, according to the present invention, the distribution of the gold nanoparticles arranged on the membrane can be controlled in a simple manner by varying the size and density of the gold nanoparticles dispersed in the aqueous solution, the pH of the aqueous solution, and the contact time of the gold nanoparticles with the membrane. Since the nanopores are formed at locations where the gold nanoparticles are arranged, their distribution and locations can be set by controlling the distribution of the gold nanoparticles.

As illustrated in FIGS. 4 and 5, nanopores with various shapes and sizes can be selectively formed by at least one factor selected from the diameter of the gold nanoparticles, the thickness of the membrane, the processing temperature, and the processing time.

The present invention will be explained in detail with reference to the following examples.

Example 1: Closed Nanopores Free of Gold Nanoparticles

A 30 nm thick silicon nitride membrane was purchased from Norcada (NT025X). The membrane was produce by depositing silicon nitride on the upper and lower surfaces of a 200 μm silicon substrate by CVD and etching one of the surfaces of the silicon substrate. A dispersion of 50-nm-diameter gold nanoparticles in an aqueous sodium citrate solution was purchased from Sigma-Aldrich. Dilute hydrochloric acid (pH 1.5), an oxygen plasma system, and a heater capable of reaching a temperature of 1050° C. were prepared.

First, the silicon nitride membrane was treated with an oxygen plasma at a 40 W power for 1 min and 50 μl of the dilute hydrochloric acid was dropped into 100 μl of the aqueous sodium citrate solution in which gold nanoparticles were dispersed, to prepare a nanoparticle solution. At this time, the sodium citrate having dispersed the gold nanoparticles in the nanoparticle solution was separated from the gold nanoparticles and slow aggregation of the gold nanoparticles was observed.

Before complete aggregation of the gold nanoparticles, the silicon nitride membrane having undergone the oxygen plasma treatment was dipped in the nanoparticle solution. When the silicon nitride membrane came into contact with the gold nanoparticles, changes in zeta potential occurred to create an attractive force between the gold nanoparticles and the silicon nitride membrane. It was found that the gold nanoparticles were randomly attached to the surface of the membrane.

~10 sec after attachment of the gold nanoparticles, the membrane attached with the gold nanoparticles was rinsed with distilled water and dried.

The dried membrane was placed in a heater, heated from room temperature to 1000° C. over ~2 h, and maintained at that temperature for ~1 h. After the heater was turned off, the process was allowed to proceed until the temperature was lowered to 950° C. with the door closed. The process did not proceed any further at 950° C. or less. Thereafter, the membrane was allowed to cool to room temperature and taken out from the heater.

As a result, the gold nanoparticles disappeared on the membrane, and instead, the membrane was perforated with open conical nanopores. The nanopores were formed at the locations where the gold nanoparticles were arranged. The silicon nitride was deformed around the entrances of the nanopores to form ring-shaped protrusions.

Example 2: Open Nanopores in which the Gold Nanoparticles Remained Attached to One Surface of the Membrane Nanopores were formed in the same manner as in Example 1, except that the silicon nitride membrane was heated at the processing temperature of the heater (1000° C.) for 1.5 h. The silicon nitride membrane, the aqueous sodium citrate solution containing nanoparticles, the dilute hydrochloric acid, the oxygen plasma system, and the heater used in this example were the same as those used in Example 1. The other conditions were maintained the same as those in Example 1.

As a result, the nanopores penetrated the membrane and the gold nanoparticles remained in portions of one surface of the membrane around the entrances of the nanopores.

Example 3: Closed Nanopores Having Inner Surfaces to which Gold Nanoparticles Remained Attached Nanopores were formed in the same manner as in Example 1, except that the silicon nitride membrane was heated at the processing temperature of the heater (1000° C.) for 50 min. The silicon nitride membrane, the aqueous sodium citrate solution containing nanoparticles, the dilute hydrochloric acid, the oxygen plasma system, and the heater used in this example were the same as those used in Example 1. The other conditions were maintained the same as those in Example 1.

As a result, the nanopores were closed in shape and had inner surfaces to which the gold nanoparticles remained attached.

Example 4: Open Nanopores Free of Gold Nanoparticles

The procedure of Example 1 was repeated except that the diameter of the gold nanoparticles was changed to 200 nm, the thickness of the silicon nitride membrane was changed to 50 nm, the gold nanoparticles were located on the silicon nitride membrane, the silicon nitride membrane was placed on the silicon substrate, the processing temperature was maintained at 1050° C. for 1 h in a CVD system, and the temperature was lowered to 900° C. for 1 h and to room temperature in the CVD system.

As a result, open nanopores free of the gold nanoparticles were formed.

Example 5

30-nm-diameter gold nanoparticles were located on a 30 nm thick silicon nitride membrane using a dispersion of the gold nanoparticles in an aqueous sodium citrate solution and dilute hydrochloric acid (pH 3.0) in the same manner as in Example 1.

Example 6

Gold nanoparticles were located on membranes in the same manner as in Example 5. The contact times of the membranes with a mixture of an aqueous sodium citrate solution and dilute hydrochloric acid were set to 5 sec and 30 sec. The distributions of the gold nanoparticles on the membranes were investigated.

The distribution of the gold nanoparticles when the contact time was 5 sec was denser than that when the contact time was 30 sec. The gold nanoparticles were present individually when the contact time was 5 sec. The gold nanoparticles aggregated in twos and threes and were sparsely distributed when the contact time was 30 sec.

Comparative Example 1

Open nanopores were formed in the same manner as in Example 4, except that the processing temperature was maintained at 1050° C. for 1.5 h.

The gold nanoparticles remained attached to one surface of the membrane, unlike in the open nanopores formed in Example 4 from which the gold nanoparticles were removed. Therefore, it can be concluded that the processing time is a factor affecting the shape of the nanopores.

Comparative Example 2

Gold nanoparticles were attached to a membrane in the same manner as in Example 5, except that the dispersion of the gold nanoparticles in the aqueous sodium citrate solution was diluted ten-fold before use.

The use of the dilute solution led to a smaller amount of the gold nanoparticles attached. Therefore, it can be concluded that the density of the gold nanoparticles is a factor determining the distribution of the gold nanoparticles arranged on the membrane.

Although the present invention has been described herein with reference to the specific embodiments, these embodiments do not serve to limit the invention and are set forth for illustrative purposes. It will be apparent to those skilled in the art that modifications and improvements can be made without departing from the spirit and scope of the invention. Such simple modifications and improvements of the present invention belong to the scope of the present invention, and the specific scope of the present invention will be clearly defined by the appended claims.

What is claimed is:

1. A method for forming nanopores comprising:
(A) preparing a dispersion of a plurality of gold nanoparticles;
(B) dipping a membrane in the dispersion to attach the plurality of gold nanoparticles to a first surface of the membrane; and
(C) heating the membrane attached with the plurality of gold nanoparticles to a predetermined processing temperature such that surface layers of the plurality of gold nanoparticles are liquefied and evaporated, to form nanopores with predetermined shapes on the membrane,
wherein the nanopores penetrate the membrane from the first surface of the membrane to a second surface of the membrane opposite to the first surface to form open shapes, or are recessed from the first surface of the membrane to form closed shapes, and
wherein at least a portion of the plurality of gold nanoparticles are removed from the membrane.

2. The method according to claim 1, wherein step (A) comprises preparing the dispersion of the plurality of gold nanoparticles in an aqueous sodium citrate solution and adding dilute hydrochloric acid to the dispersion to prepare a solution of the plurality of gold nanoparticles at a pH of 3.0 or less.

3. The method according to claim 1, wherein the membrane is a silicon nitride (SiN) or silicon oxide ($SiO_2$) membrane.

4. The method according to claim 1, further comprising treating the membrane with an oxygen plasma to clean the membrane before step (B).

5. The method according to claim 1, further comprising washing the membrane attached with the plurality of gold nanoparticles with distilled water after step (B) and prior to step (C).

6. The method according to claim 1, wherein the predetermined processing temperature is from 950 to 1060° C.

7. The method according to claim 1, wherein the nanopores have conical shapes whose cross-section decreases gradually from the first surface of the membrane attached with the gold nanoparticles to the second surface of the membrane.

8. The method according to claim 7, wherein the nanopores are formed in different shapes by at least one factor selected from diameters of the plurality of gold nanoparticles, a thickness of the membrane, and the predetermined processing temperature.

9. The method according to claim 1, wherein at least another portion of the plurality of gold nanoparticles remain attached to inner surfaces of the nanopores.

10. The method according to claim 1, wherein at least another portion of the plurality of gold nanoparticles remain attached to the first surface of the membrane.

11. The method according to claim 10, wherein diameters of the plurality of gold nanoparticles are at least 1.5 times larger than a thickness of the membrane.

* * * * *